United States Patent [19]
Gharibian et al.

[11] Patent Number: 5,697,123
[45] Date of Patent: Dec. 16, 1997

[54] FOLDING SURGICAL LIGHT HANDLE

[75] Inventors: Noel Gharibian, Glendale; Oscar Garza, Castaic, both of Calif.

[73] Assignee: Graphic Controls Corporation, Buffalo, N.Y.

[21] Appl. No.: 654,403

[22] Filed: May 28, 1996

[51] Int. Cl.$^6$ ............................................ A47B 95/02
[52] U.S. Cl. .................. 16/114 R; 206/223; 206/438; 362/804
[58] Field of Search ................ 16/114 R, 111 R; 206/223, 438; 362/804

[56] References Cited

U.S. PATENT DOCUMENTS

| | | |
|---|---|---|
| D. 298,864 | 12/1988 | Jefferson . |
| D. 313,670 | 1/1991 | Barron et al. . |
| 4,559,671 | 12/1985 | Andrews et al. . |
| 4,605,124 | 8/1986 | Sandel et al. . |
| 4,844,252 | 7/1989 | Barron et al. . |
| 4,974,288 | 12/1990 | Reasner . |
| 4,976,299 | 12/1990 | Bickelman . |
| 5,065,296 | 11/1991 | Cude . |
| 5,156,456 | 10/1992 | Hoftman et al. . |
| 5,273,157 | 12/1993 | Spina . |
| 5,355,292 | 10/1994 | Hoftman et al. . |
| 5,493,757 | 2/1996 | Horan et al. . |

OTHER PUBLICATIONS

Brochure—"Saf-T-Grip Saf-T-Handle", American Medical Manufacturing, Inc., 1 page.
Brochure—"How To Keep A Handle On Your Overhead.", Lite Handle System, Devon Industries, Inc. 1989, 1 page.
Brochure—"Devon Lite Handle System", Devon Industries, Inc., 1990, 1 page.

*Primary Examiner*—Chuck Y. Mah
*Attorney, Agent, or Firm*—Lyon & Lyon LLP

[57] ABSTRACT

A folding surgical light handle is made from an inexpensive light weight material and can be made as a single part including a handle body with a grip portion, a flange, and an integral connecting member which links the handle body and flange together through a pair of hinged connections. The hinged connecting member enables the light handle to be folded for convenient storage and to be quickly unfolded when the light handle is needed. A threaded head integral to the flange portion provides a way for the light handle to be installed on a surgical light fixture.

16 Claims, 3 Drawing Sheets

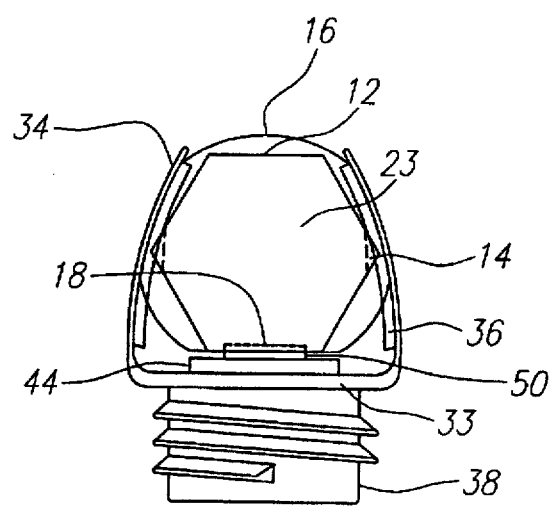
FIG. 4
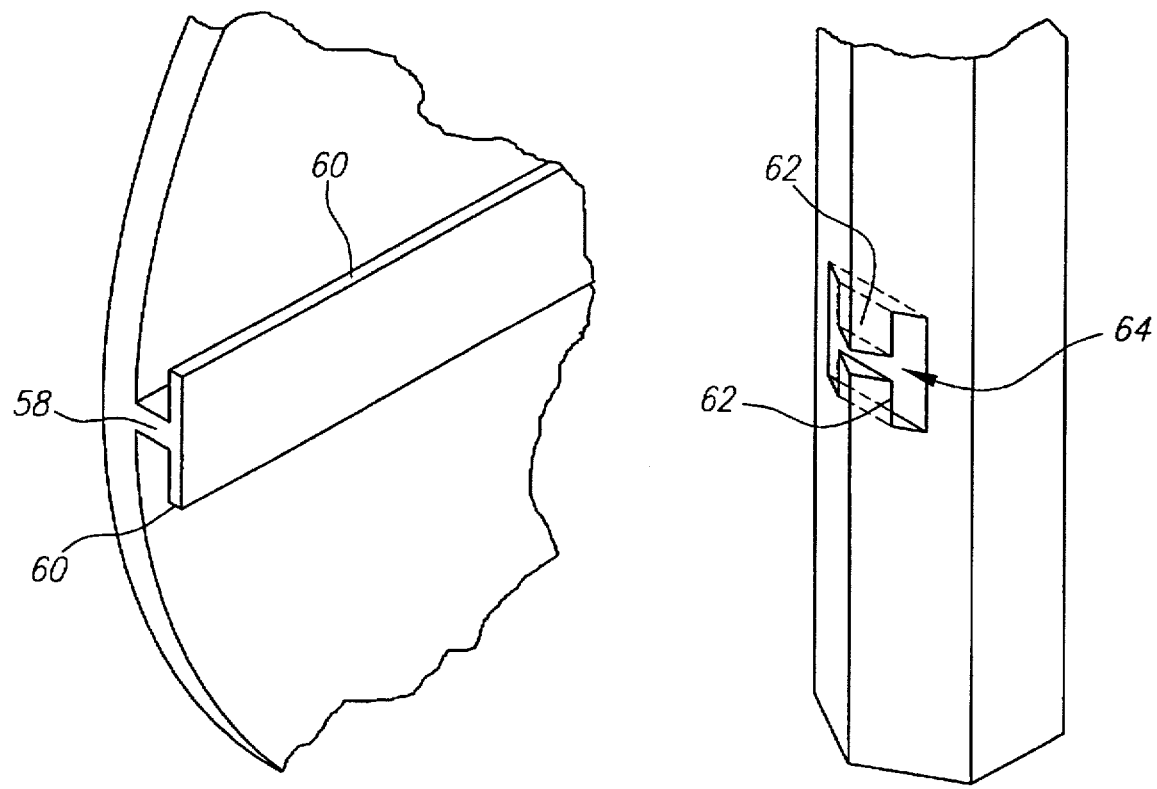
FIG. 5A
FIG. 5B

FOLDING SURGICAL LIGHT HANDLE

FIELD OF THE INVENTION

The field of the invention is disposable handles for operating room light fixtures.

BACKGROUND OF THE INVENTION

In hospital operating rooms, light fixtures are normally suspended above the operating room table to illuminate the surgical site. Typically, a surgical light fixture has a centrally positioned handle. During a surgical procedure, the position of the light fixture is often adjusted by a surgeon or nurse, using the handle. Because the surgical personnel must physically grasp the handle to adjust the fixture's position, the light fixture handle must be sterile.

Disposable light handles and handle covers are now in widespread use. Disposable light handles are preferably inexpensive and designed to be easily installed onto an operating room light fixture by hospital personnel, and then easily removed and disposed of after a surgical procedure. In addition, the handle should be capable of compact storage in a sterile packaging prior to use. While various handles and covers have been successfully used in the past, there remains a need for an improved light handle.

SUMMARY OF THE INVENTION

To these ends, a surgical light fixture handle is advantageously foldable for compact storage prior to use and can be quickly unfolded and installed by hospital personnel when needed. Preferably, the light handle has a handle body, a flange portion, and an integral connecting member which connects the handle body and flange with a pair of hinged connections. Other and further objects and advantages will appear hereinafter.

BRIEF DESCRIPTION OF THE DRAWINGS

In the drawings, wherein similar reference characters denote similar elements throughout the several views:

FIG. 4 is an end view of the folded light handle of FIG. 3 with the outer portions of the flange web being further folded against the handle body.

FIG. 5A is an enlarged view of an alternative embodiment rib.

FIG. 5B is an enlarged view of an alternative embodiment notch for making a snap fit with the rib of FIG. 5A.

DETAILED DESCRIPTION OF THE INVENTION

Figure 1:
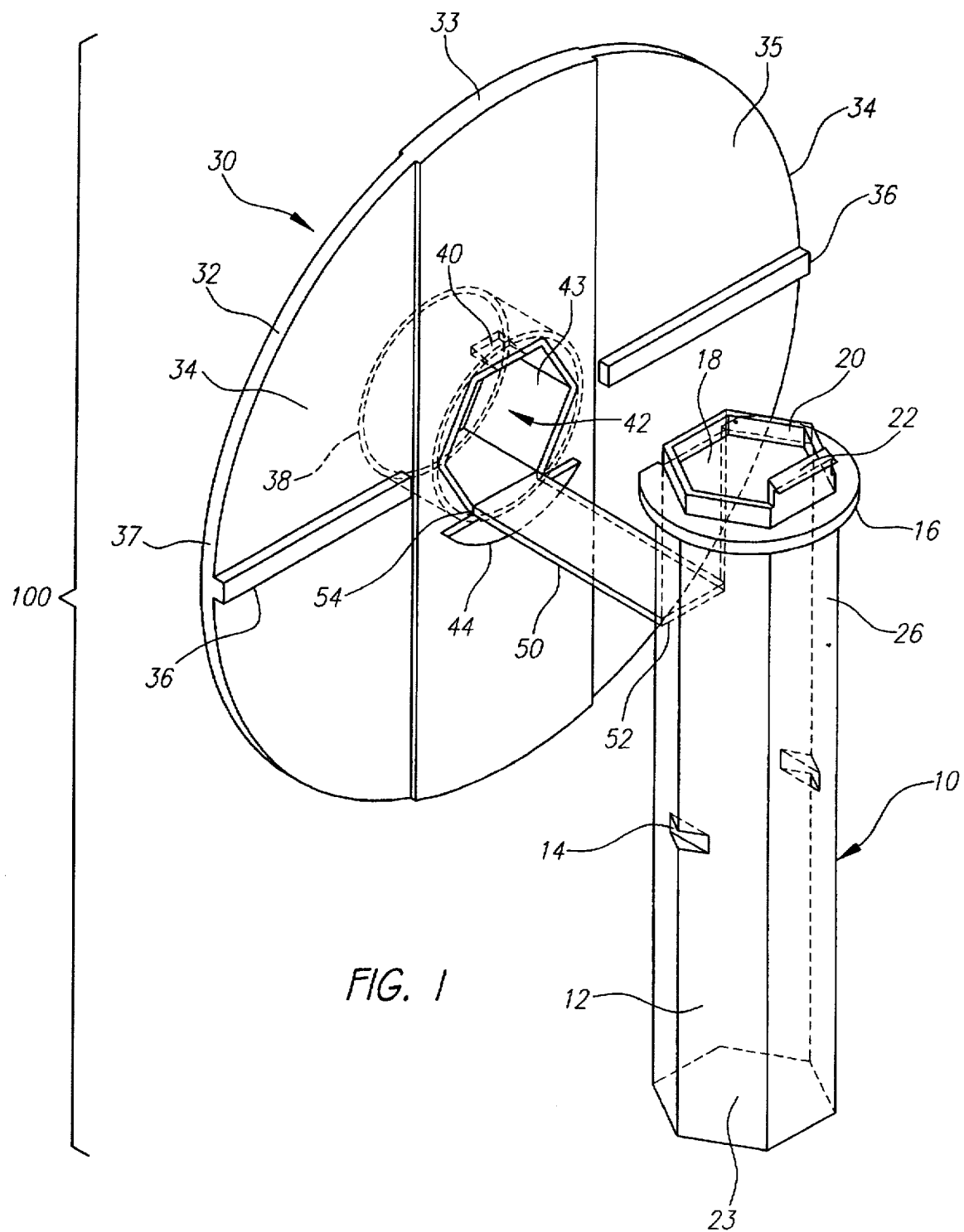
FIG. 1 is a perspective view a folding light handle with the flange portion partially folded.

Turning now in detail to the drawings, as shown in FIG. 1, a folding light handle 100 preferably is one piece. A handle body 10 and a flange 30 which are advantageously connected to each other by an integral connecting member 50 via a pair of hinged connections 52 and 54 located at opposite ends of the connecting member 50. The light handle 100 is preferably made from a light weight inexpensive injection moldable plastic material which is sterilizable and suitable for disposal after a single use.

Figure 2:
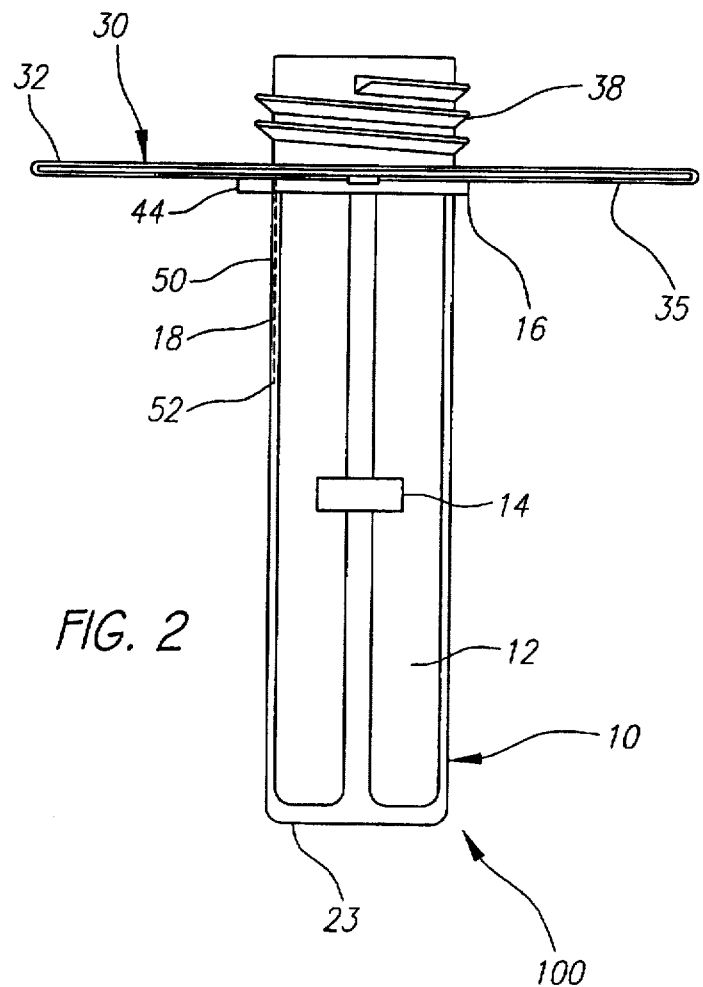
FIG. 2 is a side elevation view of the light handle of FIG. 1 with the flange portion fully unfolded.
Figure 3:
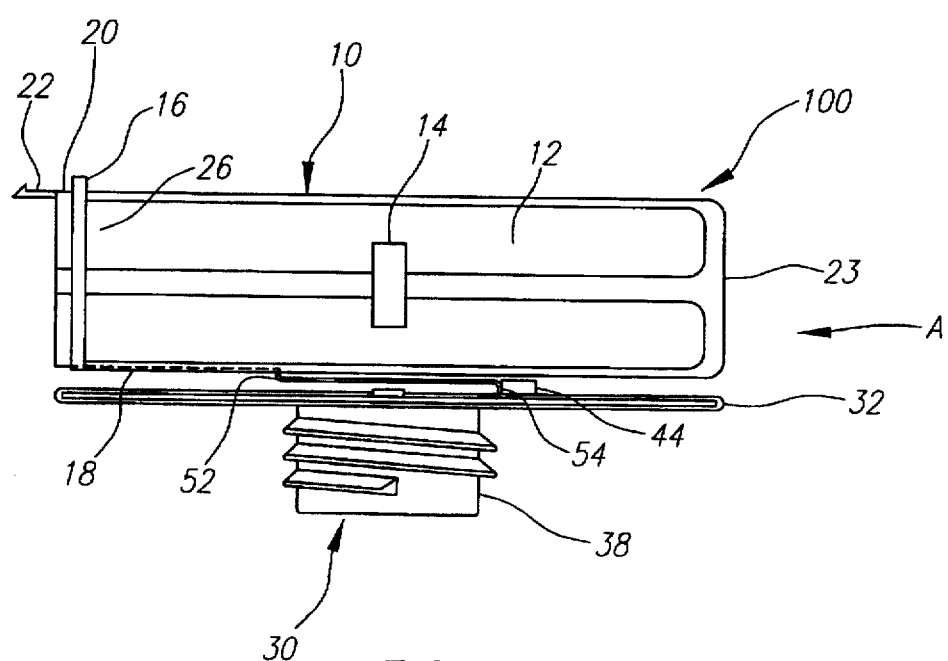
FIG. 3 is a side elevation view of the light handle of FIG. 1 with the flange portion folded against the handle body.

The handle body 10 has a grip portion 12, which is of generally hexagonal tubular construction, a generally circular collar 16 integral to an upper end 26 of the grip portion 12, and a generally hexagonal plug 20 which is integral to the grip portion 12 and protrudes beyond the collar 16. Other shapes may, of course, also be used. Integral to the plug 20 is a detent 22. A lower end 23 of the grip portion 12 is closed. The grip portion 12 further includes a slot 18 which is advantageously positioned to receive the connecting member 50 when the flange portion is fully unfolded as shown in FIG. 2. As shown in FIGS. 1–4, notches 14 are provided on opposite sides of the grip portion 12.

The flange 30 of the light handle 100 includes an annular web 32 and an externally threaded head 38 centrally located on the web 32. The head 38 provides a way of attaching the light handle 100 to a surgical light fixture (not shown). Through the head 38 and web 32 of the flange 30 is a central opening 42 which is sized to receive the plug 20 of the handle body 10. On an interior surface 43 in the opening 42 is a locking step 40 which is positioned to engage the detent 22 when the flange 30 is fully unfolded as in FIG. 2.

In a preferred embodiment, the web 32 is relatively flexible and has ribs 36 on a bottom surface 35 of the web 32. When the flange 30 is fully folded as in FIG. 3, the web 32 may be further folded around the handle body 10 so that the ribs 36 can be snap fitted into the notches 14 as shown in FIG. 4 enabling the light handle 100 to be packaged and stored compactly.

The web 32 has a somewhat rectangular middle section 33 with curved short sides or edges and wings or outer sections 34, which are shaped as chords. The wings 34 are relatively thinner and more flexible than the middle section 33, which is more rigid. As shown in FIG. 1, the thinner wings are vertically centered on the middle section, with small steps on the top and bottom surfaces of the web 32 where the wings join the middle section. The ribs 36 are located on the outer sections 34 and provide additional stiffness for the web 32. The ribs 36 extend radially inwardly from an outer edge 37 of the web 32 and stop before reaching the middle section 33. This allows the web 32 to remain flexible enough to fold as shown in FIG. 4. When the flange 30 is fully unfolded, the collar 16 fits in the space between the ribs 36. In this fully unfolded position, the collar 16 closes off the central opening 42 and provides additional stiffness to the portion of the web 32 between the ribs 36. As shown in FIGS. 1–4, a portion of the generally circular collar 16 facing the connecting member 50 is flattened to prevent interference during the unfolding of the light handle 100. A step 44 is located on the web 32 which corresponds to the flattened portion of the collar 16. The collar on the handle forces the wings 34 on the flange into a generally horizontal position.

Turning to FIGS. 5A and 5B, preferably, the wings are snap fit onto the handle, for compact and easier packaging using a modified rib 58 and notch or slot 62. A friction fit may be provided by the rib 36 and notch 14 shown in FIG. 1 to hold the wings 34 onto the handle. However, snap fit features, such as a lip 60 and tabs 62 provide a positive snap fit. As shown in FIGS. 5A and 5B, as the wings 34 are folded down and pressed against the handle, the lips 60 will snap through the tabs 62. The tabs 62 then hold the wings alongside the handle, with the rib 58 in the slot 62. Of course, various other mechanical equivalent snap features may be used, such as clip, button, stud, dovetail, and latch features, etc. Similarly, various other ways of holding the wings to the handle without a snap feature, as in FIG. 1, may be used, such as inherent material spring force or memory, adhesives, velcro, molded material tacking, etc.

Thus, while various features have been shown and described, various modifications may, of course, be made and various equivalents substituted in, without departing from the spirit and scope of the invention.

We claim:

1. A folding, surgical light handle comprising:
   (a) a handle body including a grip portion;
   (b) a flange; and
   (c) a connecting member pivotably attached to the handle body via a first hinged connection at a first end of the connecting member and pivotably attached to the flange via a second hinged connection at a second end of the connecting member.

2. The light handle of claim 1 wherein the flange further comprises a circular web and an externally threaded head attached to the web.

3. The light handle of claim 2 wherein at least part of the circular web is flexible.

4. The light handle of claim 3 wherein the circular web further comprises an external rib, and the grip portion of the handle body further comprises a notch positioned to receive the rib when the web is folded.

5. The light handle of claim 4 wherein the external ribs are configured to snap fit into the notches on the handle body.

6. The light handle of claim 2 wherein the web has a middle section and a pair of outer sections pivotably joined to the middle section.

7. The light handle of claim 1 wherein the light handle is one piece.

8. A folding, surgical light handle comprising:
   (a) a handle body comprising a generally cylindrical grip portion, a collar integral to an upper end of the grip portion, and a plug protruding beyond the collar;
   (b) a flange comprising a web portion having a central opening sized to receive the plug; and
   (c) a connecting member attached to the handle body with a first hinged connection and attached to the flange with a second hinged connection.

9. The light handle of claim 8 wherein the flange further comprises an externally threaded head attached to the web.

10. The light handle of claim 8 wherein the web portion of the flange is flexible.

11. The light handle of claim 10 wherein the web portion of the flange further comprises external ribs, and the grip portion of the handle body further comprises notches positioned to receive the ribs when the web is folded.

12. The light handle of claim 11 wherein the external ribs are configured to snap fit into the notches on the handle body.

13. The light handle of claim 8 wherein the handle body further comprises a detent integral to the plug where the detent fits into and engages a locking step on the flange portion when the light handle is unfolded.

14. A surgical light handle comprising:
   (a) a rigid handle body comprising a generally tubular grip portion having a pair of notches, a generally circular collar integral to an upper end of the grip portion, and a plug protruding beyond the collar and a detent integral to the plug; and
   (b) a flange comprising a flexible annular web portion with a pair of external ribs, a threaded head integral to the web, a central opening through the web adapted to receive the plug and a locking step on an interior surface within the central opening positioned to engage the detent of the plug; and
   (c) a connecting member attached to the handle body with a first hinged connection and attached to the flange with a second hinged connection.

15. The light handle of claim 14 wherein the web portion of the flange has a middle section and outer sections having different thicknesses with the outer sections being thinner and more flexible than the central section.

16. A folding, surgical light handle comprising:
   (a) a handle body including a grip portion;
   (b) a flange;
   (c) a connecting member pivotably attached to the handle body and to the flange; and
   (d) means for snap fitting the flange onto the handle body.

* * * * *